United States Patent [19]

Spranger et al.

[11] Patent Number: 4,990,251
[45] Date of Patent: Feb. 5, 1991

[54] RESILIENT SEALING RING

[75] Inventors: Kurt Spranger, Ammerbuch; Roland Antoni, Hechingen-Boll; Joachim Lutterbeck, Hechingen; Gerd Ott, Burladingen; Herbert Raabe, Haigerloch-Stetten; Josef Volm, Haigerloch-Owingen, all of Fed. Rep. of Germany

[73] Assignee: Gambro Dialystoren GmbH & Co. KG, Fed. Rep. of Germany

[21] Appl. No.: 376,135

[22] Filed: Jul. 6, 1989

[30] Foreign Application Priority Data

Jul. 7, 1988 [SE] Sweden .................................. 8802542

[51] Int. Cl.$^5$ .............................................. B01D 63/04
[52] U.S. Cl. .............................. 210/321.8; 210/321.89; 210/500.23
[58] Field of Search ................ 210/232, 321.6, 321.64, 210/321.72, 321.77, 321.78, 321.79, 321.8, 321.81, 321.87, 321.88, 321.89, 321.9, 195.2, 257.2, 500.23, 450, 451

[56] References Cited

U.S. PATENT DOCUMENTS 4,225,440 9/1980 Pitesky .............................. 210/451

Primary Examiner—Frank Sever
Attorney, Agent, or Firm—Lerner, David, Littenberg, Krumholz & Mentlik

[57] ABSTRACT

Resilient sealing rings are disclosed including an annular ring of resilient material having a cross-sectional configuration so that when not compressed the cross section of the sealing ring extends substantially longitudinally and when compressed between two parallel sealing surfaces the sealing ring bends so that the longitudinal ends approach each other. This provides acceptable compression force between the parallel sealing surfaces over an extended range of deformation particularly as compared to conventional O-rings. The use of such sealing rings in filtration and/or diffusion devices is also described, particularly in diffusion devices including a bundle of hollow fibers arranged longitudinally within a housing in which the fiber ends are embedded in end walls and in which a lid including an inlet or outlet for fluid which is intended to flow through the hollow fibers covers the end wall and in which these resilient sealing rings are positioned between the outside of the end walls and the inside of the lid.

13 Claims, 4 Drawing Sheets

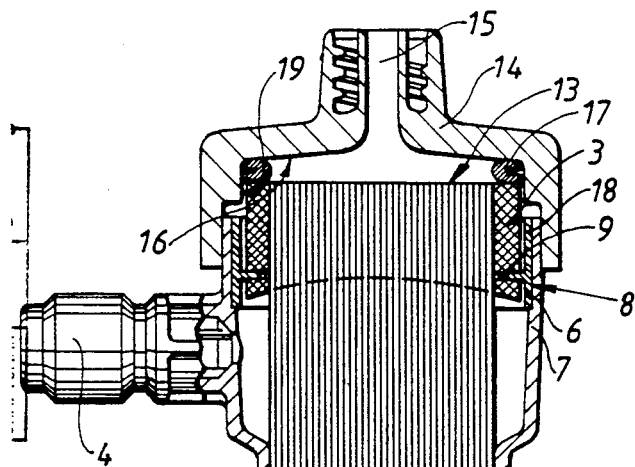
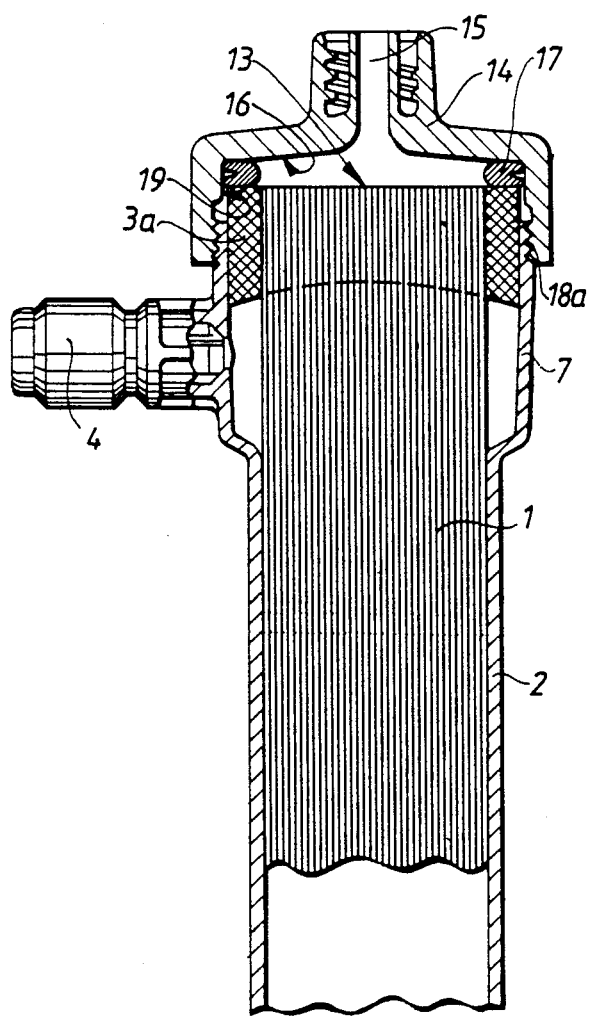

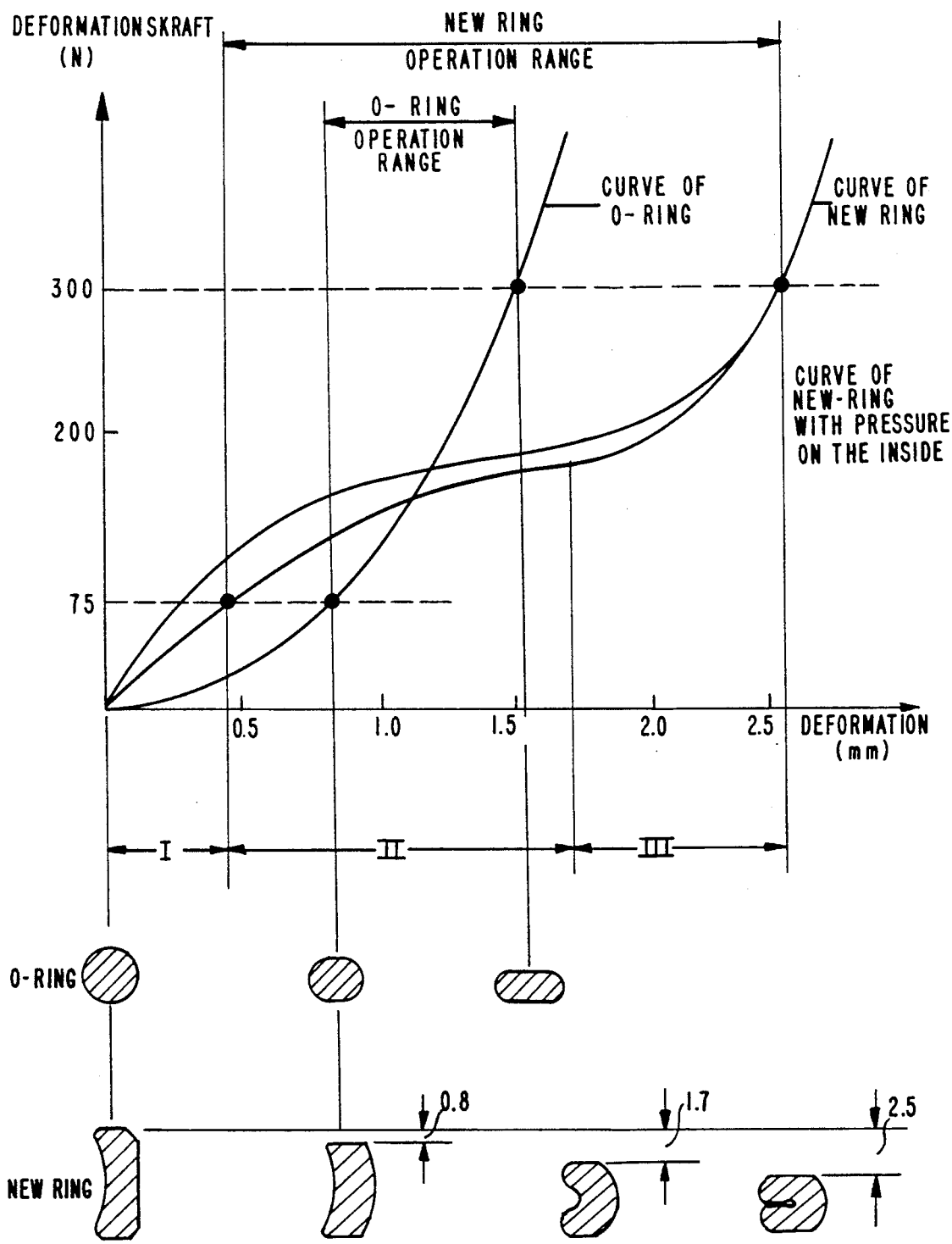

RESILIENT SEALING RING

FIELD OF THE INVENTION

The present invention relates to a seal. More particularly, the present invention relates to a sealing ring of resilient material. Still more particularly, the present invention relates to a sealing ring which is intended to be compressed between two preferably flat, parallel surfaces. Still more particularly, the present invention relates to seals which are preferably intended to be used in filtration and/or diffusion devices, in particular those, for example, as shown in U.S. Pat. application Ser. No. 07/237,514 filed on Aug. 26, 1988, pending and U.S. Pat. No. 07/237,504 filed on Aug. 26, 1988, pending which devices employ a bundle of hollow fibers arranged longitudinally within a housing and in which the ends of the fibers are embedded in end walls with the sealing ring positioned between the outside of at least one of the end walls and a lid which has an inlet and/or an outlet for liquid which is intended to flow through the hollow fibers in the bundle.

BACKGROUND OF THE INVENTION

In various filtration and diffusion devices, including those in the above-identified U.S. patent applications, these devices generally have a sealing ring which is in the form of an O-ring arranged between an end wall and a cup-shaped lid member therefor. It has been found in practice, however, that it is extremely difficult to provide exactly the required degree of tightening pressure in these devices when using such O-rings. This is particularly true when the lid is to be welded to the housing. Therefore, in order to obtain the desired degree of tightening pressure the lid must be placed in a special position regarding the housing within extremely narrow limits.

One type of sealing ring which is disclosed in the prior art is shown in French Patent No. 2,088,735. However, this type of sealing ring cannot provide the improved deformation in response to various deformation forces over a wide range thereof. Another type of sealing ring is disclosed in Swedish Patent No. 392,640. In this case, as with the aforementioned French patent, it includes an inwardly directed concave surface. Furthermore, the sealing ring is not compressed between a pair of parallel surfaces, but is compressed by a sloping surface, which thus provides characteristics of deformation in response to deformation forces which are limited to deformation by bending in only a small portion of the sealing ring, with the shape of the sealing ring maintained relatively constant by the shape of the housing within which it is maintained. It is, therefore, an object of the present invention to solve these prior difficulties which have become rather common for a number of different technical fields. Thus, it will be understood that particular advantage can be achieved by using the seals of this invention in connection with these types of filtration and/or diffusion devices, although one of ordinary skill in this art will recognize that these seals can be used advantageously for other purposes.

SUMMARY OF THE INVENTION

In accordance with the present invention the applicants have discovered a sealing ring comprising an annular ring of resilient material which has a cross-sectional configuration such that in its uncompressed condition the sealing ring has a substantially longitudinally extending configuration between first and second ends thereof including a longitudinal dimension which is greater than its transverse dimension, whereby upon being compressed between two parallel sealing surfaces the sealing ring bends in a manner such that the first and second ends approach each other and provide acceptable compression force between the parallel sealing surfaces over an extended range of deformations.

In accordance with a preferred embodiment of the sealing ring of the present invention the sealing ring bends in a manner such that the first and second ends approach each other in a direction external to the sealing ring, whereby upon being compressed between the two parallel sealing surfaces and a third outer surface which is substantially perpendicular to those parallel surfaces, the sealing ring presents a concave configuration facing the third sealing surface.

In a preferred embodiment of the sealing ring of the present invention, in its uncompressed condition the substantially longitudinally extending configuration includes an arcuate shape, thereby providing concave and convex outer surfaces, with the concave outer surface facing outwardly from the sealing ring.

In another embodiment of the sealing ring of the present invention in its uncompressed condition the substantially longitudinally extending configuration includes a pair of concave outer surfaces, whereby upon being compressed between the two parallel sealing surfaces one of the concave outer surfaces becomes substantially planar.

In accordance with another embodiment of the present invention applicants have discovered a sealing ring comprising an annular ring of resilient material having a cross-sectional configuration such that upon being compressed between two parallel sealing surfaces the sealing ring bends into a compressed configuration in which the compression force increases gradually at a first rate and above a predetermined compression force the compression force is increased at a second rate which is accelerated as compared to the first rate. In a preferred embodiment, as the sealing ring is being bent into its compressed configuration, the compression force increases at a third rate which is also accelerated as compared to the first rate. In a highly preferred embodiment the relationship of the compression force to the deformation of the sealing ring is substantially as shown in FIG. 5 hereof.

In accordance with another embodiment of the sealing ring of the present invention, the cross-sectional configuration of the sealing ring is such that in its uncompressed condition the sealing ring has a substantially longitudinally extending configuration between first and second ends thereof which includes a longitudinal dimension which is greater than its transverse dimension.

In accordance with another embodiment of the present invention, applicants have also discovered a diffusion/filtration device, which can preferably be such a device for dialysis, hemofiltration, hemodiafiltration or oxygenation, and which comprises a housing defining a longitudinally extending internal chamber including a first end and a second end, a bundle of semi-permeable hollow fibers disposed within the internal chamber, the hollow fibers extending longitudinally from the first end of the housing to its second end, and having an outer surface and a first end and a second end which correspond, respectively, to the first and second ends of the housing, lid means for attachment to the first end of the housing, the lid means including fluid communication means for providing fluid to or withdrawing fluid from the first end of the internal chamber, end wall means supporting the first end of the hollow fibers within the internal chamber to sealingly separate the first end of the hollow fibers from the outer surface of the hollow fibers between the first and second ends thereof, and a sealing ring disposed between the end wall means and the lid means and comprising an annular ring of resilient material having a cross-sectional configuration such that in its uncompressed condition the sealing ring has a substantially longitudinally extending configuration between first and second ends thereof including a longitudinal dimension which is greater than its transverse dimension, whereby upon being compressed between the end wall means and the lid means the sealing ring bends in such a manner that the first and second ends approach each other.

In a preferred embodiment the lid means has a cup-shaped configuration including a peripheral flange which is adapted to be attached to the external surface of the first end of the housing, and preferably this is done by welding, glueing or screwing the lid means to the housing. In a preferred embodiment the sealing ring is an elastomeric material such as rubber.

It can be seen that the sealing ring of the present invention has a form such that as it is compressed it quickly reaches a knicking or bending position, in the area defined by region I in FIG. 5, from which the compression force increases slowly as compared with the initial state of compression, in the area defined by region II in FIG. 5, eventually reaching a position from which the compression force once again increases at a more rapid rate, in the area defined by region III in FIG. 5. By employing such a sealing ring it is now possible to alter the position of the lid vis-a-vis that of the housing particularly in the types of filtration/diffusion devices mentioned above within rather wide limits and at the same time still obtain small changes of the compression force as is discussed in more detail below, particularly in reference to the drawings.

In the above-described preferred embodiment of the sealing ring of the present invention in which a third outer sealing surface enclosing the sealing ring is employed, a liquid under pressure within the sealing ring will tend to press the sealing ring against that third sealing surface, thus providing an improvement in the tightness of the seal provided by the sealing ring in that the same liquid pressure will provide increased sealing pressure at the same time against the first two parallel sealing surfaces perpendicular to this third sealing surface.

In accordance with the embodiment of the sealing ring of the present invention in which a concave outer surface is provided directed against the third sealing surface, yet another advantage is realized in that parallel sealing is obtained along two parallel lines at the third sealing surface which is parallel to the two opposed sealing lines against the first and second parallel sealing surfaces.

In accordance with a preferred embodiment of the sealing ring of the present invention, it has a configuration prior to compression such as that shown in FIG. 3, which can be a boomerang or C-shaped configuration. In this embodiment the concave side of the sealing ring is directed outwardly against the third sealing surface, and in this manner a convex side of the sealing ring is obtained directed inwardly or toward the center of the sealing ring. If this convex side of the sealing ring is to be exposed to an inner pressure, it will be more or less flattened or planar, which is advantageous especially when the liquid within the sealing ring is a perishable liquid such as blood. This tendency of this preferred sealing ring can be further strengthened by including an indentation (see FIG. 4) on the convex side of the sealing ring, i.e., one having a form such that this side of the sealing ring will obtain an essentially flat form perpendicular to the first and second parallel sealing surfaces in the sealing position of the sealing ring.

As is also mentioned above, significant advantages are realized when the sealing ring of the present invention is used as part of a filtration and/or diffusion device as discussed above, such as a dialyzer. As is discussed above, the sealing ring in this case can have a construction such that it exhibits very gentle influences on the liquid, such as blood, passing through the sealing ring. In comparison with normal O-rings, the typical wedge-formed gaps above and below the sealing ring where it contacts the first and second substantially parallel surface is not obtained. As is also mentioned above, because of this configuration the lid for the filtration/diffusion device can be manufactured with far greater tolerances than has previously been the case, and this is particularly true for lids which are intended to be welded to the housings thereof. Under normal circumstances, such a lid which is intended to be welded to the housing must be made within very narrow tolerances since the welding machine restricts the possibility of placing lids of different dimensions in different positions so as to provide a desired degree of tightening pressure.

The resilient sealing ring of the present invention is preferably made of rubber or a similar elastomeric material. However, other materials can be used if they are provided with a form and resiliency so as to provide the above-described functions.

BRIEF DESCRIPTION OF THE DRAWINGS

FIG. 1 is a partial, partially sectional, elevational view of a filtration and/or diffusion device including the sealing ring of the present invention;

FIG. 2 is a partial, partially sectional, elevational view of a modified filtration and/or diffusion device including a sealing ring according to the present invention;

FIG. 5 is a graphical representation showing the deformation for various deformation forces for a normal O-ring and for the sealing ring according to the present invention.

DETAILED DESCRIPTION

Figure 3A:
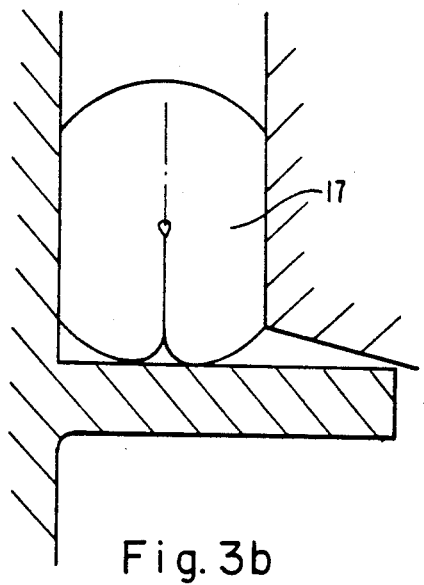
FIGS. 3a through 3c are cross-sectional, elevational views of a sealing ring according to the present invention subjected to three different degrees of compression.

Turning to the Figures, in which like numerals refer to like elements thereof, FIG. 1 shows one end of a filtration and/or diffusion device of the type disclosed in the above-identified U.S. patent application Ser. No.

07/237,504, but provided with a sealing ring 17 according to the present invention. The device consists of a bundle of hollow fibers 1 arranged in a housing 2 with the ends embedded in a potting material providing an end, wall 3. The ends of the fibers have been opened by a transverse cut providing an end surface 13, as described, for example, in U.S. Pat. No. 4,689,191. The device is provided with an inlet and/or outlet 4 and a second outlet and/or inlet 15 for first and second liquids, respectively. Normally, the other end of the device (not shown in the drawings) is given an identical form. However, if the device is intended to be used only for filtration, a second nipple 4 is unnecessary.

The nipple 4 serving as an inlet or an outlet is arranged on an enlarged portion 7 of the housing 2. Within this enlarged portion 7, there is located a ring 6 in a groove 8, the ring 6 including an inner flange 9 which serves to reduce the contact area between the end wall 3 and the housing 2, as is described in more detail in the above-identified U.S. patent application. For that purpose the ring 6 is made of a material which has a coefficient of adhesion with regard to the material of the end wall which is less than the coefficient of adhesion of the housing with regard to the same material of the end wall.

The inlet and/or outlet 15 is arranged in a lid 14 which is attached to the enlarged portion 7 of the housing 2 by a welding 18. Alternatively, it may be attached by glue.

The two above-mentioned parallel sealing surfaces are provided by end surface 13 of the fiber bundle 1 on the one hand and by the inside 16 of the lid 14 on the other. The third sealing surface is designated 19, and is provided by the inside of the flange of the lid 14.

Referring next to FIG. 2, there is shown a more conventional filtration and/or diffusion device modified in accordance with the present invention. Many details of FIG. 2 are essentially identical to corresponding details of FIG. 1, and have therefor been given the same reference numerals. Consequently, the device according to FIG. 2 comprises a bundle of hollow fibers 1 within a housing 2 with an enlarged portion 7 to which a lid 14 is attached. The attachment is, however, not made by glue or welding, but in this case by means of a screw connection 18a. The end surface of the fiber bundle has been designated 13, and the fiber ends have been opened in the same manner as is described above. The device includes inlets and/or outlets 4 and 15, and a sealing ring 17 according to the present invention in the same way as the device described above. An end wall 3a made by a potting material, contrary to the end wall 3, has a strong attachment to the inner wall of the enlarged portion 7 of the housing 2.

In order to explain the function of the sealing ring 17, reference is made to FIGS. 3a to 3c, FIGS. 4a to 4c, and to FIG. 5. In an uncompressed condition the ring may, for example, have cross-sectional configuration as shown in either FIG. 3c or FIG. 4c with the upper side being intended to be directed inwardly against the liquid passing through the inlet and/or outlet 15 in both cases.

Figure 4A:
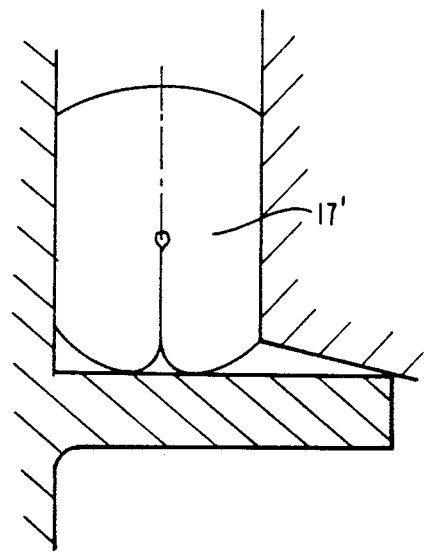
FIGS. 4a through 4c are cross-sectional, elevational views of another embodiment of the sealing ring of the present invention exposed to three different degrees of compression.
Figure 3B:
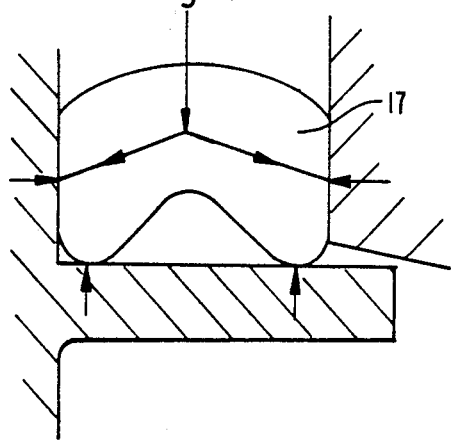
Figure 4B:
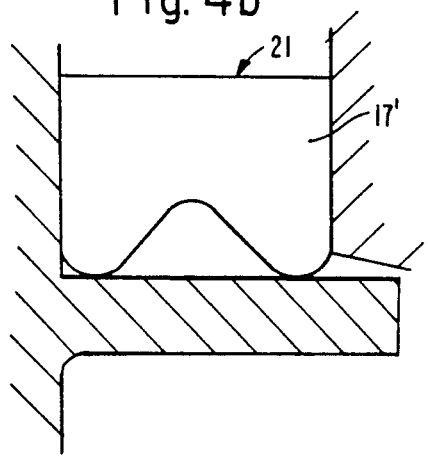
Figure 3C:
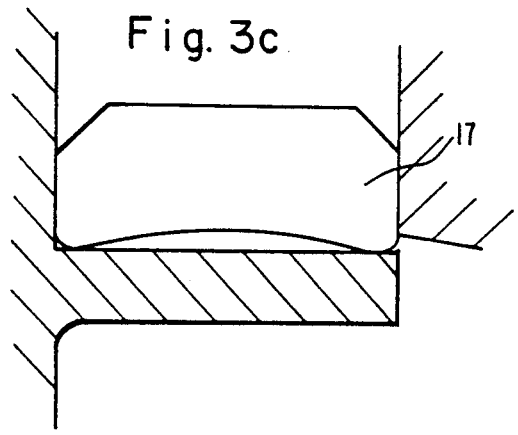
Figure 4C:
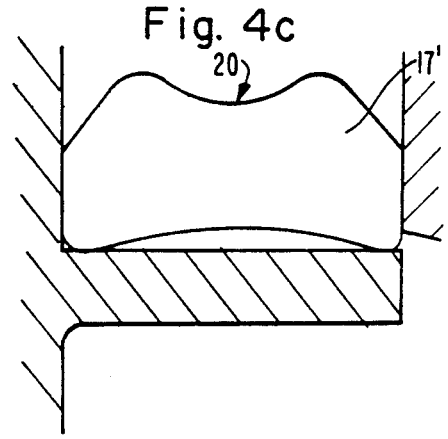

FIGS. 3b and 4b show the same cross-sections through the sealing ring in an ideal sealing position. The flat surface 21 shown in FIG. 4b of the modified sealing ring 17' according to FIGS. 4a to 4c is provided by means of the indentation 20 shown in FIG. 4c.

By means of the application of further compression the positions shown in FIGS. 3a and 4a are eventually reached, and a good seal is still provided thereby. However, thereafter, further compression will rapidly increase the deformation force in an unacceptable manner.

FIG. 5 shows the deformation as a function of the deformation force for a normal O-ring on the one hand, and a sealing ring according to the present invention on the other. This comparison is presented in the form of an example. By using different materials and dimensions, the figures in FIG. 5 will, of course, vary. In the example shown, a normal O-ring may be used within a range of operation of between 0.8 and 1.6 mm, corresponding to deformation forces of between 75 and 300 N. A sealing ring according to the present invention, however, reaches an acceptable sealing pressure much more rapidly, i.e., after about 0.4 mm, and the deformation force is still below the acceptable 300 N up to a deformation of about 2.5 mm. Consequently, according to the present invention, it is possible to use lids, housings, sealing rings and welding tools or other tools for attachment, and to do so within wide tolerances.

Figure 6:
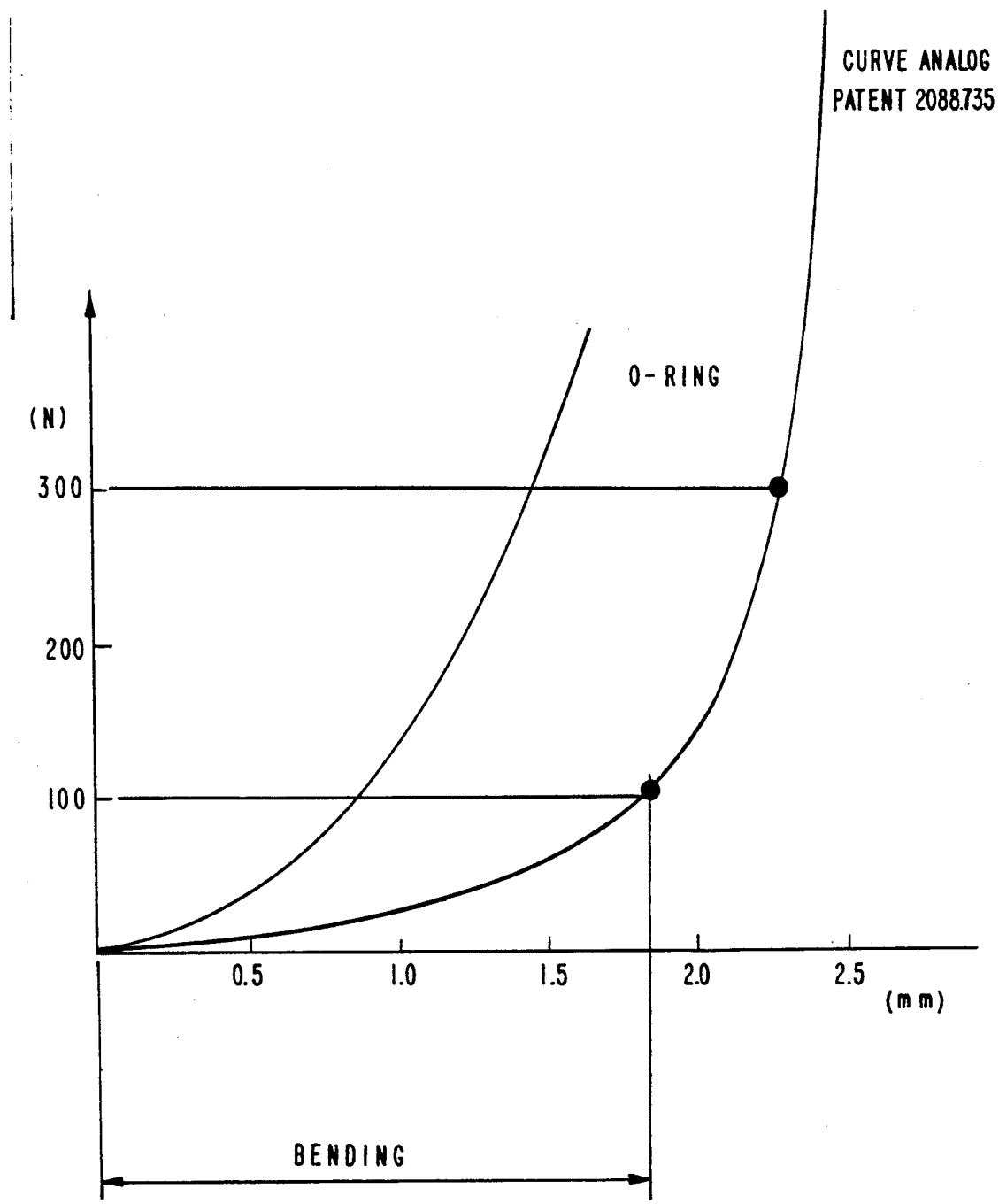
FIG. 6 is a graphical representation showing the deformation for various deformation forces for a normal O-ring and for the type of sealing ring shown in French Patent No. 2,088,735.

FIG. 6 shows the deformation as a function of the deformation force for a normal O-ring and for the sealing ring shown in French Patent No. 2,088,735. As can be seen therein, and particularly as compared to the characteristic curve of the sealing ring of the present invention as shown in FIG. 5, the characteristic curves in FIG. 6 show similar slow decreases in the force at low deformations which then increase rapidly at higher deformations. Thus, in their area of operation, they show deformations which mainly relate to deformation by bending, somewhat like that in area II of the sealing ring of the present invention. They do not, however, exhibit the overall characteristics of the sealing rings of the present invention, including that of the areas designated I and III in FIG. 5 hereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A diffusion/filtration device comprising
   a housing defining a longitudinally extending internal chamber including a first end and a second end,
   a bundle of semi-permeable hollow fibers disposed within said internal chamber, said hollow fibers extending longitudinally from said first end of said housing to said second end of said housing, said hollow fibers having an outer surface and a first end and a second end corresponding, respectively, to said first end and said second end of said housing,
   lid means for attachment to said first end of said housing, said lid means including fluid communication means for providing fluid to or withdrawing fluid from said first end of said internal chamber,
   end wall means supporting said first end of said hollow fibers within said internal chamber so as to sealingly separate said first end of said hollow fibers from said outer surface of said hollow fibers between said first and second ends thereof, and
   sealing ring means for providing acceptable compression force between said end wall means and said lid means over an extended range of deformations, said sealing ring means comprising an annular ring of resilient material having a cross-sectional configuration such that in its uncompressed condition said sealing ring has a substantially longitudinally extending configuration between first and second ends thereof including a longitudinal dimension which is greater than its transverse dimension, whereby upon being compressed between said end wall means and said lid means said sealing ring bends in a manner such that said first and second ends approach each other.

2. The diffusion/filtration device of claim 1 wherein said sealing ring bends in a manner such that said first and second ends approach each other at a location external to said sealing ring, whereby upon being compressed between said lid means and said end wall means and a third outer sealing surface substantially perpendicular to said lid means and said end wall means said sealing ring presents a concave configuration facing said third sealing surface.

3. The diffusion/filtration device of claim 1 wherein in said uncompressed condition said substantially longitudinally extending configuration includes an arcuate shape, thereby providing concave and convex outer surfaces, with said concave outer surface facing outwardly from said ring.

4. The diffusion/filtration device of claim 1 wherein in said uncompressed condition said substantially longitudinally extending configuration includes a pair of concave outer surfaces, whereby upon being compressed between said two parallel sealing surfaces one of said concave outer surfaces of said sealing ring becomes substantially planar.

5. The diffusion/filtration device of claim 1, said sealing ring having a cross-sectional configuration such that upon being compressed between said means and said end wall means said sealing ring bends into a compressed configuration in which the compression force increases gradually at a first rate and above a predetermined compression force said compression forces increase at a second rate, said second rate being accelerated with respect to said first rate.

6. The diffusion/filtration device of claim 5 wherein as said sealing ring is being bent into said compressed configuration said compression force increases at a third rate, said third rate being accelerated with respect to said first rate.

7. The diffusion/filtration device of claim 6 wherein the relationship of said compression force to the deformation of said sealing ring is substantially as shown in FIG. 5 hereof.

8. The diffusion/filtration device of claim 5 wherein said cross-sectional configuration is such that in its uncompressed condition said sealing ring has a substantially longitudinally extending configuration between first and second ends thereof including a longitudinal dimension which is greater than its transverse dimension.

9. The diffusion/filtration device of claim 8 wherein upon being compressed between said lid means and said end wall means said sealing ring includes a concave surface facing outwardly from said sealing ring.

10. The diffusion/filtration device of claim 9 wherein said lid means has a cup-shaped configuration including peripheral flange means adapted to be attached to the external surface of said housing at said first end thereof.

11. The diffusion/filtration device of claim 10 wherein said peripheral flange means of said lid means is attached to said first end of said housing by a method selected from the group consisting of welding, gluing and screw means.

12. The diffusion/filtration device of claim 9 wherein said sealing ring comprises an elastomeric material.

13. The diffusion/filtration device of claim 12 wherein said sealing ring comprises rubber.

* * * * *

UNITED STATES PATENT AND TRADEMARK OFFICE
CERTIFICATE OF CORRECTION

PATENT NO. : 4,990,251

DATED : February 5, 1991

INVENTOR(S) : SPRANGER ET AL.

It is certified that error appears in the above-identified patent and that said Letters Patent is hereby corrected as shown below:

ON THE TITLE PAGE:

[30] Foreign Application Priority Data-- "8802542" should read --88.02542-4--.

Column 8, line 26, delete "Claim 9" and insert therefor --Claim 1--.

Column 8, line 35, delete "Claim 9" and insert therefor --Claim 1--.

Signed and Sealed this

Thirteenth Day of October, 1992

*Attest:*

DOUGLAS B. COMER

*Attesting Officer*  *Acting Commissioner of Patents and Trademarks*